US00PP22777P2

(12) United States Plant Patent
Skelton

(10) Patent No.: US PP22,777 P2
(45) Date of Patent: Jun. 12, 2012

(54) ***ACTINIDIA CHINENSIS* PLANT NAMED 'W47'**

(50) Latin Name: *Actinidia chinensis*
Varietal Denomination: W47

(76) Inventor: Donald Skelton, Rangiriri (NZ)

( * ) Notice: Subject to any disclaimer, the term of this patent is extended or adjusted under 35 U.S.C. 154(b) by 0 days.

(21) Appl. No.: 12/928,375

(22) Filed: Dec. 9, 2010

(51) Int. Cl.
*A01H 5/00* (2006.01)

(52) U.S. Cl. ..... Plt./156
(58) Field of Classification Search ..... Plt./156
See application file for complete search history.

*Primary Examiner* — Annette Para
(74) *Attorney, Agent, or Firm* — Cassandra Bright

(57) ABSTRACT

A new and distinct *Actinidia chinensis* cultivar named 'W47' is disclosed, characterized by having distinctive yellow flesh fruit, and a very late seasonal harvest time in New Zealand. Additionally, the new variety produces fruit with very soft, downy pubescence and with a distinctive blunt, slightly protruding stylar end shape and square shoulders. The new variety is suitable for commercial production of kiwi fruit.

3 Drawing Sheets

Latin name of the genus and species: *Actinidia chinensis.* Variety denomination: 'W47'.

BACKGROUND OF THE INVENTION

The new cultivar is a product of a planned breeding program begun in 1975 under the direction of the inventor, Donald Alfred Skelton, a citizen of New Zealand. The seed parent is the unpatented, proprietary seedling variety referred to as *Actinidia chinensis* 'R5' The pollen parent is the unpatented, proprietary seedling variety referred to as *Actinidia chinensis* 'RY.'

Fruit of the new variety was first evaluated in 2001 with favorable results. After the first evaluation, semi-hardwood cuttings were made of 'W47' and were grafted onto 5 seedling rootstocks 3; of *A. chinensis* and 2 of *A. deliciosa.* Evaluation, asexual propagation and grafting all first took place at the inventor's commercial nursery in Rangiriri, New Zealand. Subsequent evaluations of the variety have shown the characteristics to be true to type.

SUMMARY OF THE INVENTION

The cultivar 'W47' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'W47' These characteristics in combination distinguish 'W47' as a new and distinct *Actinidia chinensis* cultivar:

1. Distinctive yellow flesh fruit.
2. Very late season harvest during May under New Zealand conditions.
3. Very soft, downy pubescence on fruit.
4. Ovoid fruit shape.
5. Fruit with a distinctive square shoulders.
6. Moderate adherence of skin to the fruit.

COMPARISON TO PARENT

Plants of the new cultivar 'W47' are similar to plants of the seed parent, *Actinidia chinensis* 'R5' in most horticultural characteristics, however, plants of the new cultivar 'W47' produce fruit several weeks earlier than 'R5'. Additionally, 'W47' produces larger fruit than 'R5'. Average fruit size of 'W47' is 105 grams compared to 75 gram fruit from 'R5'.

Plants of the new cultivar 'W47' are similar to plants of the male parent, *Actinidia chinensis* 'RY' in some horticultural characteristics. However, as the sex expression of 'RY' is male, plants of 'RY' produce only male flowers, whereas the sex expression of 'W47' is female, and plants produce female flowers that in turn develop into large fruit.

COMMERCIAL COMPARISON

The new variety is best compared to the commercial variety, 'Hort16A,' U.S. Plant Pat. No. 11,066. 'W47' is similar to 'Hort16A' in many horticultural characteristics, however, 'W47' produces mature fruit later in the season than 'Hort16A.' Additionally, fruit of the new variety 'W47' are distinctively blunt, with only slight protusion on the stylar end, compared to the strong pointed stylar end shape of 'Hort16A.' Fruit shape differences can also be noted in the shoulder shape. Whereas 'W47' produces fruit with strongly squared shoulder, 'Hort16A' fruit have rounded shoulders.

BRIEF DESCRIPTION OF THE PHOTOGRAPH

The accompanying photograph in FIG. 1 illustrates in full color typical foliage, hanging fruit and stems on plants of 'W47.'

DETAILED BOTANICAL DESCRIPTION

Figure 1:
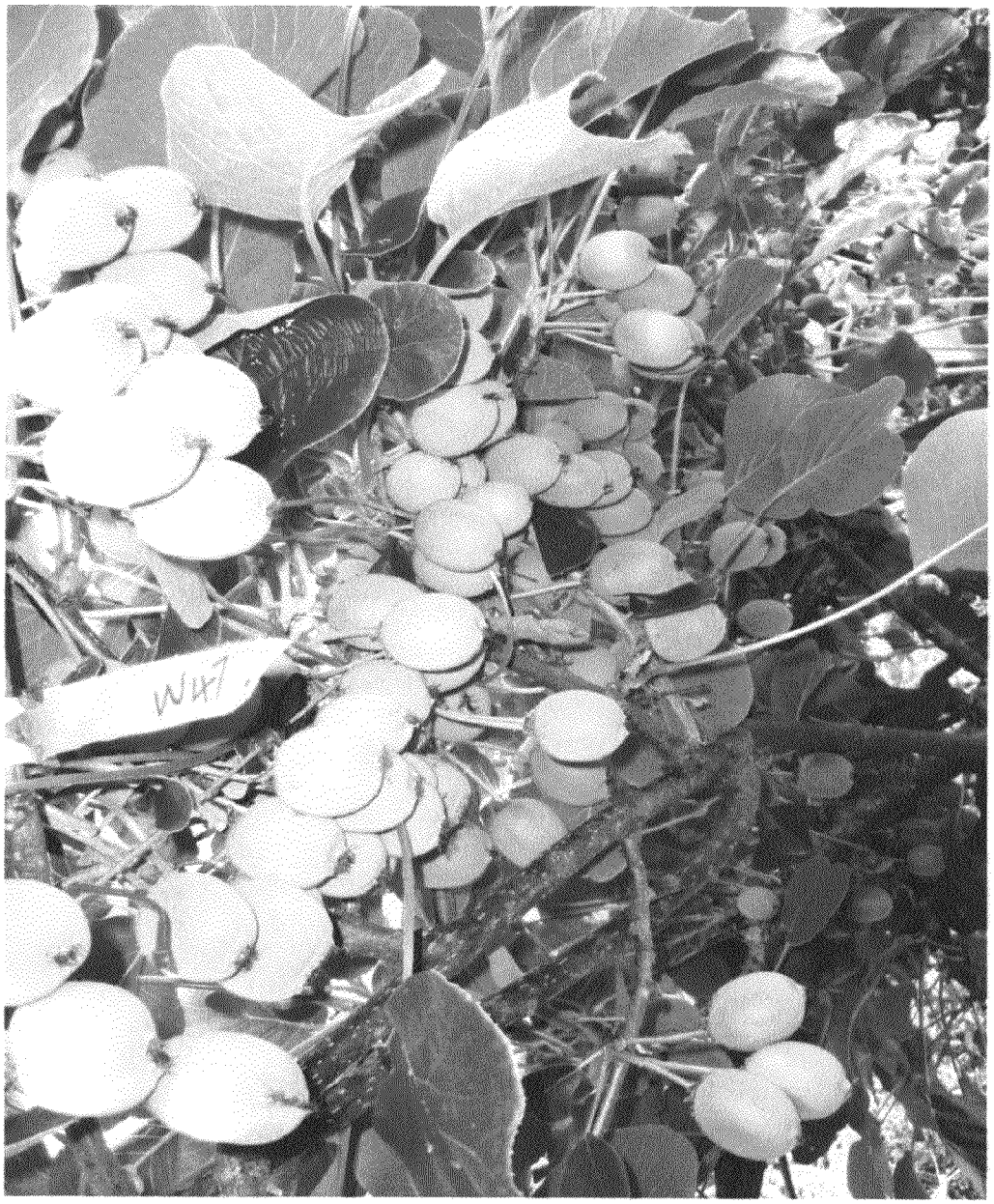
Figure 2:
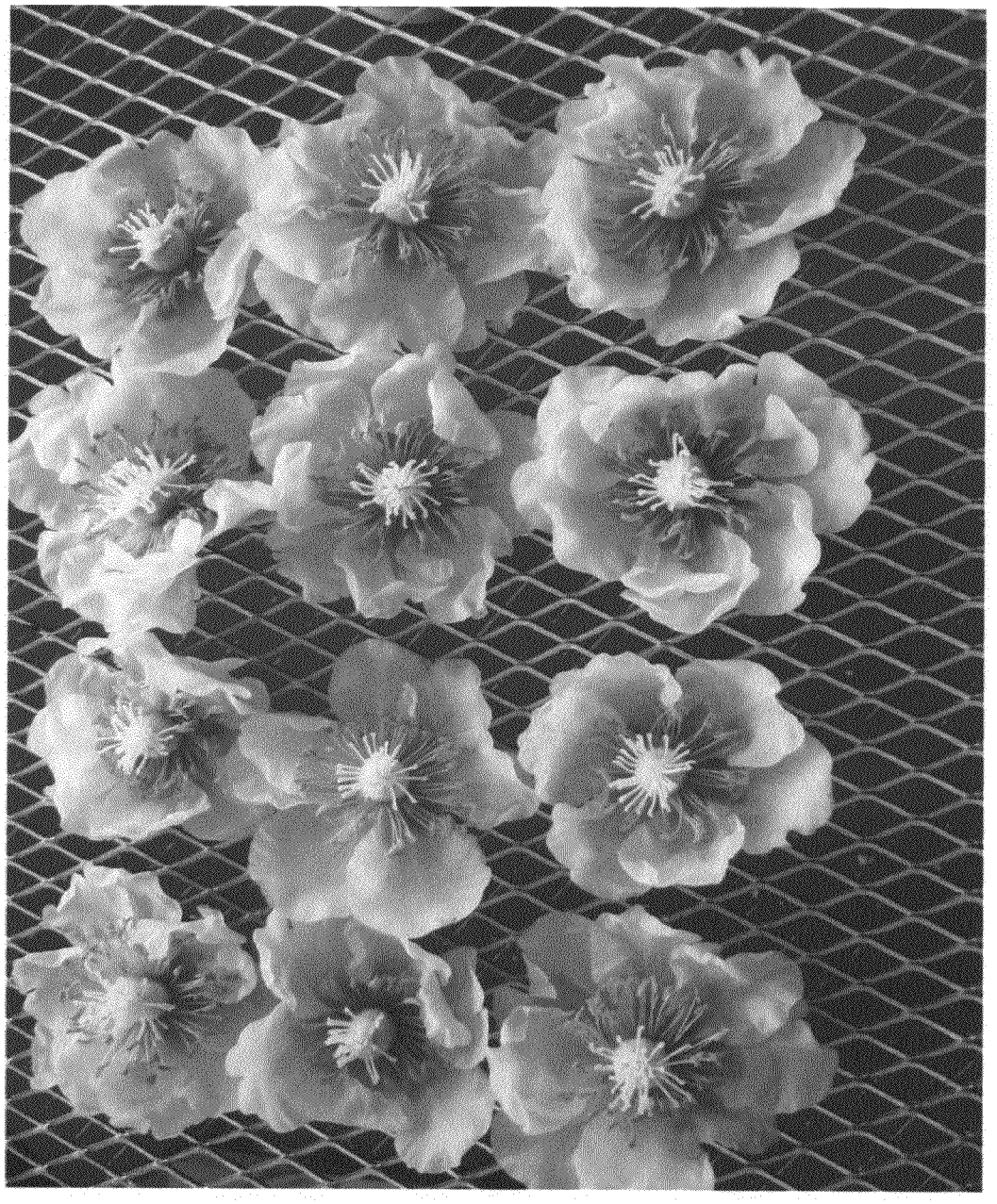
FIG. 2 illustrates in full color typical flowers of 'W47.'
Figure 3:
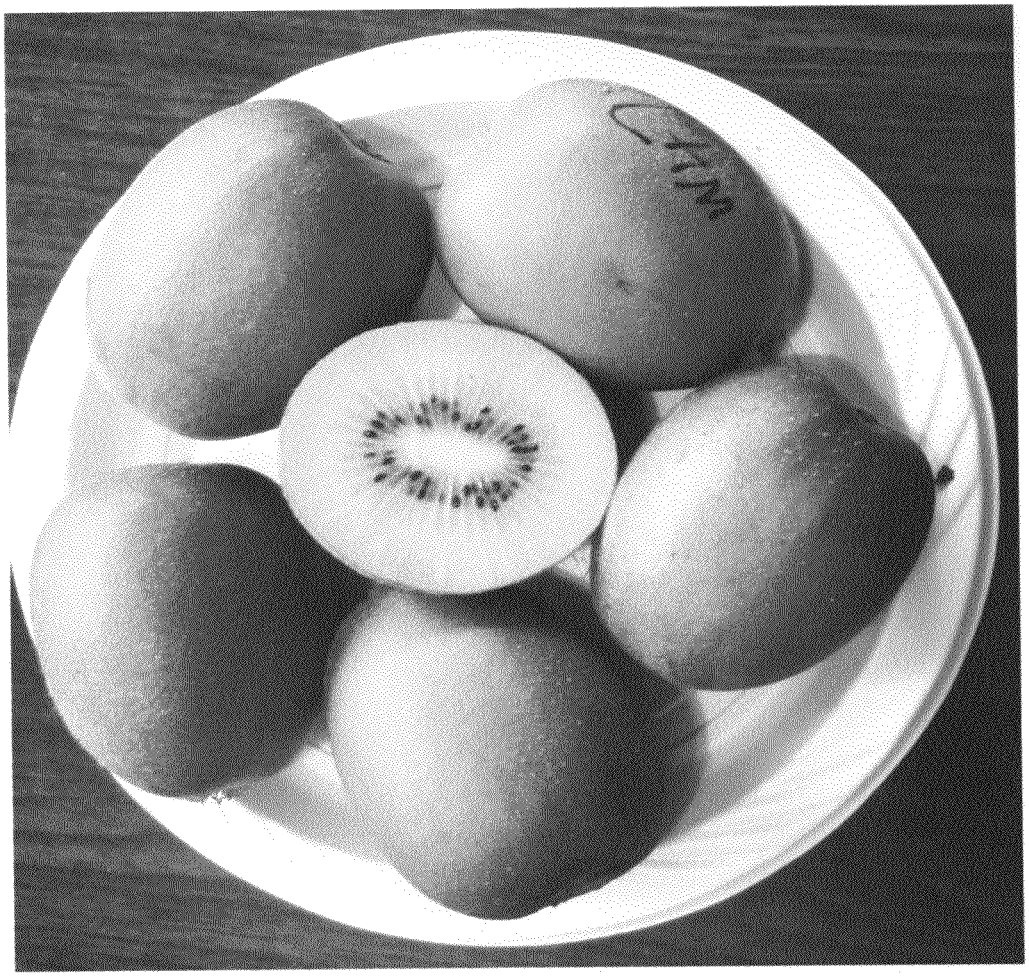
FIG. 3 shows examples of typical fruit harvested from 'W47.' All photographs are taken of plants approximately 9 years old. The photographs were taken using conventional techniques and although colors may appear different from actual colors due to light reflectance it is as accurate as possible by conventional photographic techniques.

In the following description, color references are made to The Royal Horticultural Society Colour Chart except where general terms of ordinary dictionary significance are used.

The following observations and measurements describe 'W47' plants grown outdoors under commercial trial conditions in Rangiriri New Zealand. The growing temperature ranged from 10° C. to 30° C. during the day and −4° C. to 18° C. at night. Annual rainfall is approximately 125 cm per year. Measurements and numerical values represent an average of 10 typical plant types.

Botanical classification: *Actinidia chinensis* 'W47.'

PROPAGATION 'W47' can be successfully grafted onto rootstocks of *Actnidia chinensis* or *Actinidia deliciosa.*

PLANT

*Age of the plant described.*—Approximately 9 years.
*Sex expression.*—Female.
*Ploidy.*—Diploid.
*Vigor.*—Moderate.
*Young shoot color.*—Near RHS Yellow-Green 144B.
*Young shoot texture.*—Smooth, non-pubescent and no visible lenticels.
*Stem diameter.*—Average 1.5 cm.
*Stem texture.*—Rough.
*Trunk diameter.*—Average 12 cm on a 11 year old plant.
*Stem lenticels.*—Irregularly spaced and sized. Oblong in shape, color near RHS Grey-Green 191 A.

FOLIAGE

Leaf:
*Average length.*—18 cm.
*Average width.*—18.5 cm.
*Shape of blade.*—Very broadly ovate.
*Apex.*—Rounded.
*Base.*—Cordate, overlapping.
*Attachment.*—Petioled.
*Margin.*—Ciliate.
*Texture of top surface.*—Slightly puckered. Non-pubescent.
*Texture of under side.*—Non-pubescent.
*Color.*—Mature foliage upper side: Near RHS Green N138A. Mature foliage under side: Near RHS Green 138B.
*Petiole.*—Length: Average length 12.5 cm. Pubescence: None. Color: Upper Surface near RHS Red 39B, lower surface near Orange-Red 31D.

FLOWER

*Flowers per inflorescence.*—Normally 1, occasionally 3.
*Bud color.*—Near RHS Yellow-Green 145A.
*Bud break.*—End of August.
*First flower.*—Early October.
*Diameter.*—Average 6 cm.
*Petal quantity.*—6 to 10 per flower.
*Petals overlapping.*—Yes.
*Color.*—Near RHS White 155A.
*Filament color.*—Near RHS White 155A.
*Anther color.*—Near RHS Greyed-Orange 163D.
*Attitude of styles.*—Semi-erect.
*Style color.*—Near RHS White 155A.
*Style quantity.*—Average 18.
*Hair on ovary.*—Dense.
*Color of ovary.*—Near RHS White 155A.
*Number of sepals.*—6 to 10.
*Color of sepals.*—Near RHS Yellow-Green 145A.
*Sepal width.*—Approximately 1 cm.
*Sepal length.*—Approximately 1.3 cm.
*Sepal texture.*—Smooth.

Peduncle:
*Length.*—Average 6.6 cm.
*Color.*—Near RHS Yellow-Green 145A.
*Texture.*—Smooth.

FRUIT

*Color outer pericarp.*—Near RHS Yellow 3C.
*Color inner pericarp.*—Near RHS Yellow 3A.
*Core color.*—Near RHS White 155A.
*Brix at consumption.*—18.0.
*Brix at harvest.*—7.50%.
*Average weight.*—105 grams.
*Minimum weight.*—91 grams.
*Maximum weight.*—124 grams.
*Length.*—Avg. 7.6 cm.
*Width.*—Avg. 6.4 cm.
*Core diameter (maximum).*—2.6 cm.
*Core diameter (minimum).*—1.0 cm.
*Locule number.*—38.
*Fruit peduncle length.*—6.6 cm.
*Fruit peduncle width.*—6.4 cm.
*General shape.*—Ovoid.
*Median cross section.*—Circular.
*Stylar end shape.*—Slightly blunt protruding.
*Shoulder shape.*—Squared.
*Calyx ring.*—Present.
*Calyx ring expression.*—Strong.
*Skin color at harvest.*—Near RHS Yellow-Green 153B.
*Hair on fruit skin.*—Downy.
*Hair adherence to skin.*—Moderate.
*Skin adherence to flesh at maturity.*—Moderate.
*Fruit core shape.*—Transversely elliptic.
*Core-woody spike.*—Small.
*Lenticels on fruit.*—Minute, moderate in quantity, colored near RHS Yellow-Green 153A.
*Mature seed color.*—Black.
*Dried seed.*—Brown.
*Harvest time.*—Early May in New Zealand.
*Overall cropping quantity.*—30 to 50 tons per hectare.

OTHER CHARACTERISTICS

Storage life.—Storage life is a minimum of 3 months at 2° C.
Disease/pest resistance.—Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'W47' as herein illustrated and described.

* * * * *